[19] United States Patent
Jacques et al.

[11] Patent Number: 5,723,143
[45] Date of Patent: Mar. 3, 1998

[54] SOLID MUCOADHESIVE THERAPEUTIC OR HYGIENIC COMPOSITION FOR APPLICATION TO THE BUCCAL OR NASAL MUCOUS MEMBRANE

[75] Inventors: Yves R. Jacques, Annecy, France; Claude Gaillard, Lyngby, Denmark; Pierre Buri, Troinex, Switzerland; Bernard Boisrame, Lure, France; Catherine Aubry, Lure, France; Vassilios Kaltsaltos, Lure, France

[73] Assignee: Vetoquinol S.A., Lure, France

[21] Appl. No.: 755,348

[22] Filed: Nov. 25, 1996

Related U.S. Application Data

[63] Continuation of Ser. No. 344,674, Nov. 21, 1994, abandoned.

[30] Foreign Application Priority Data

Nov. 24, 1993 [FR] France .................. 93 14057

[51] Int. Cl.$^6$ .................. A61K 9/20; A61K 9/40
[52] U.S. Cl. .................. 424/435; 424/434; 424/464; 424/478; 424/480; 424/484; 424/487; 424/489
[58] Field of Search .................. 424/464, 478, 424/480, 434, 435, 484, 487, 489

[56] References Cited

U.S. PATENT DOCUMENTS 4,226,848 10/1980 Nagai et al. .................. 424/19

FOREIGN PATENT DOCUMENTS

| 0 020 777 | 1/1981 | France . |
| 0 107 941 | 5/1984 | France . |
| 2 571 253 | 4/1986 | France . |
| 51-26127 | 3/1976 | Japan . |

OTHER PUBLICATIONS

Database WPI, Section Ch, Week 7616, Derwent Publications Ltd., London, GB; Class A03, AN 76-29041x.

*Primary Examiner*—Thurman K. Page
*Assistant Examiner*—Sharon Howard
*Attorney, Agent, or Firm*—Oliff & Berridge, P.L.C.

[57] ABSTRACT

Solid mucoadhesive therapeutic or hygienic composition, for human or veterinary use, intended to be administered by application to the buccal or nasal mucous membrane, containing, in a mixture, 15 to 25% by weight of a cellulosic ether gelifiable in the presence of an aqueous liquid, 10 to 15% by weight of a homopolymer or copolymer of acrylic acid or a physiologically acceptable salt thereof, 30 to 45% by weight of a gelatin, and one or more therapeutic or hygienic active constituents. The cellulosic ether preferably is a $C_1$–$C_4$ alkyl ether of cellulose, a $C_1$–$C_4$ hydroxyalkyl ether of cellulose, or mixtures thereof.

9 Claims, No Drawings

SOLID MUCOADHESIVE THERAPEUTIC OR HYGIENIC COMPOSITION FOR APPLICATION TO THE BUCCAL OR NASAL MUCOUS MEMBRANE

This is a Continuation of application Ser. No. 08/344,674 filed Nov. 21, 1994, now abandoned.

The present invention relates to a solid mucoadhesive therapeutic or hygienic composition, for human or veterinary use, intended to be administered by application to the buccal or nasal mucous membrane, this composition comprising, in a mixture, a cellulosic ether gelifiable in the presence of an aqueous liquid, a homopolymer or copolymer of acrylic acid or a physiologically acceptable salt of that homopolymer or copolymer, and at least one therapeutic or hygienic active constituent.

Although the mixture of a cellulosic ether gelifiable in an aqueous medium with a homo- or copolymer of acrylic acid does in itself reveal good mucoadhesive properties, it is however difficult to produce industrially, from this mixture, solid shapes such as tablets, for example. As a matter of fact, and particularly because of problems of material handling (sticking) and of the poor flow properties of this mixture, which are substantially due to the polymer of acrylic acid, manufacturing operations in producing tablets are laborious, and it is difficult to obtain tablets of constant quality and which are perfectly reproducible. Moreover, tablets made from such a mixture have a tendency to swell intensely under the effect of aqueous liquids (saliva for example); this may not only compromise the cohesion of these tablets, but can also, when the latter are applied to the buccal mucous membrane, cause disturbance in the oral cavity, a disturbance against which the subject under treatment, particularly if an animal is involved, tends to react by applying the tongue against the tablet, which by this fact undergoes premature erosion.

One of the aims of the present invention is to remedy these drawbacks, and to this end it proposes a composition in accordance with that defined in the first paragraph of this description, and which is characterised in that it comprises, as said cellulosic ether, 15 to 25% by weight of an element selected from the group comprising $C_1$–$C_4$ alkyl ethers of cellulose, $C_1$–$C_4$ hydroxyalkyl ethers of cellulose and their mixtures and 10 to 15% by weight of the said homopolymer, copolymer or salt, and in that it also comprises 30 to 45% by weight of gelatin.

It has in effect been noted that, by means of the combination of cellulosic ether, of a polymer of acrylic acid and of gelatin in the specific proportions mentioned above, it is possible to eliminate the drawbacks of previously-known conventional compositions. Thus the polymer of acrylic acid, by reason of its extremely fine granularity, will be capable of effecting a physical coating of the particles of gelatin. Separation of the particles will diminish their static charge and therefore reduce the frictional and adhesive forces between these particles when they are handled, with the effect of improving the flow of the mixture of cellulosic ether and polymer of acrylic acid, and of enabling simple reproducible manufacture of the composition according to the invention.

Formation of a complex by attraction of the negative charges of the polymer or copolymer of acrylic acid and the positive charges of the gelatin in an acid medium ensures that cohesion of the tablet is retained, and opposes excessive swelling of the composition according to the invention when the latter is brought into contact with an aqueous liquid.

It should be added that, despite the presence of the gelatin (which by its nature is a very average mucoadhesive) at a relatively high concentration (30–45%) within the composition according to the invention, the latter retains in a surprising way adhesive properties which are quite remarkable, since it may be kept in mucoadhesion in the buccal cavity for at least 4 to 8 hours, a period entirely sufficient for the said composition to exert its therapeutic or hygienic effects in an efficient manner.

In addition, it is well known that gelatin, when it is used alone, forms in an aqueous medium a gel which erodes rapidly. It is entirely unexpected that, when it is associated (even at such high proportions as 45% by weight) with the two other ingredients of the composition according to the invention, it makes possible the obtention of a composition (tablets, for example) with a cohesion which is entirely sufficient with regard to the erosive activity of the various aqueous liquids to which it is subjected in situ.

The cellulosic ether contained in the composition according to the invention forms in the presence of an aqueous liquid a viscous matrix which is insoluble and hydrophilic, and ensures progressive and thus prolonged release of the active constituent or constituents of the composition. Gelatin, because of its hydrophilic character, contributes to this effect of prolonged release, while the polymer of acrylic acid reduces the rate of release of the active constituent or constituents. It follows that the association of these three ingredients in the above specific proportions enables the speed of release of the active constituent or constituents to be modulated in order to obtain release of the latter during the entire time when the composition is in situ.

The gelatin used in accordance with the invention is advantageously a type A gelatin which, in an aqueous solution of 6.67% (w/v) has a gel strength of 50–300 degrees Bloom, preferably 200–250 degrees Bloom.

The particle size of the gelatin used is advantageously less than 250 µm, preferably less than 150 µm, and is most preferably of the order of 100 µm.

A gelatin complying with these characteristics is for example a type A gelatin from pork skin available from SANOFI BIO INDUSTRIES under the mark Gelatine AT 700 T100.

The cellulosic ether used according to the invention is advantageously a hydroxypropyl cellulose or a hydroxypropylmethyl cellulose, whose molecular weight may be located in the range of 13,000 to 140,000.

Moreover, the cellulosic ether advantageously has a viscosity measured at 20° C. in a 2% (w/v) aqueous solution of the order of 10 to 75,000 mPa.s., preferably 10 to 15,000 mPa.s and most preferably of 500 to 4,000 mPa.s.

Moreover, the cellulosic ether has a degree of etherification which is preferably comprised between 0.1 and 6 or better between 1.2 and 3.

Finally, the particle size of the cellulosic ether shall advantageously be less than 500 µm, and more preferably between 150 and 250 µm.

As cellulosic ethers there will be cited for example hydroxypropyl methylcelluloses made commercially available by the DOW company under the trade marks METHOCEL E and METHOCEL K and particularly under the trade marks METHOCEL E4M, METHOCEL K15M, METHOCEL K4M and METHOCEL K100M.

The homopolymer or the copolymer of acrylic acid may be used in the form of a salt, particularly of a physiologically acceptable alkali metal salt, as a salt of sodium, of potassium or ammonium.

The particle size of the polymer or copolymer of acrylic acid or of the salt of this polymer or copolymer is advantageously from 3 to 20 µm and preferably from 3 to 10 µm.

According to the invention, preference is given to the copolymer of acrylic acid and allyl sucrose, with a molecular weight preferably comprised between 450,000 and 4,000,000, and having advantageously a viscosity measured at 25° C. in a 0.5 % (w/v) aqueous solution of 300 to 400 mPa.s. Such a copolymer is available under the trade mark CARBOPOL 934P from the B. F. Goodrich Chemical Company.

The active constituent of the composition will be selected as a function of the ailment to be treated. The following will be involved in particular:

- all active constituents having a prophylactic or curative effect on buccal and nasal pathological conditions, and in particular those requiring direct contact with the active constituent (for example, antiseptics such as chlorhexidine and its salts; antibiotics such as spiramycin; local anaesthetics such as lidocaine; anti-inflammatories such as tolfenamic acid; anti-aphtha agents; enzymes such as lysozyme, alpha-chymotrypsin; liquefiers; expectorants, etc. . .);
- all active constituents for bucco-dental hygiene; and
- all active constituents having an action by contact and particularly those capable of being decomposed when they are administered orally or parenterally (certain tonicardiacs, neuroleptics).

The composition according to the invention may contain one or more active constituents, and their proportion in the composition will be sufficient to procure the required therapeutic or hygienic action.

Apart from the abovementioned ingredients, the composition according to the invention may comprise various additives such as a vehicle (or bulk ingredient) such as starch, microcrystalline cellulose, lactose, sorbitol, mannitol, a phosphate; a lubricant such as magnesium stearate, glycerol behenate, talc, hydrogenated ricin oil or waxes (up to 5% by weight of the composition); a flow agent such as colloidal silica (up to 3% by weight of the composition); aromas, whether encapsulated or not, flavouring agents, sugaring or sweetening agents and in a general way all substances capable of improving taste, odour or appearance of the composition, these aromas, factors, agents and substances being capable of representing a total of up to 10% by weight of the composition.

The composition according to the invention is preferably used in the form of tablets which may be obtained, for example, by mixing all the ingredients (preferably in an atmosphere with a relative humidity not above 50%), until a homogeneous powder is obtained, and producing the latter in the form of tablets by direct compression. The tablets may in particular have the shape of flat discs with a thickness for example of the order of 1-3 mm and with a diameter equal to or less than 12 mm.

It is however desirable to prepare these tablets by means of a procedure comprising a compression stage preceded by a granulation stage making use of an organic non-aqueous solvent, particularly an alcohol, preferably isopropyl alcohol. In effect it has been noted from theological studies that, by putting into effect such a granulation operation, the flow of the mixture obtained for compression is greatly improved without affecting the good adhesive quality of the tablets obtained. More precisely, this procedure may comprise mixing the active constituent or constituents, the cellulosic ether, the homopolymer or copolymer of acrylic acid or a physiologically acceptable salt of the latter and gelatin until a homogeneous powder is obtained, addition to this powder of an organic non-aqueous solvent, particularly an alcohol, preferably isopropyl alcohol, granulation of the powder with the said solvent thus added, drying of the resultant granules, screening of the dried granules, addition of any additives such as a bulk ingredient and a lubricant, and compression.

The composition according to the invention may likewise be used in the form of granules obtained by granulation of the powder obtained by mixing in a homogeneous manner all the ingredients, or also in the form of this powder itself.

Moreover, the composition according to the invention may be used by placing it at any point on the buccal or nasal mucous membrane [preferably at a point where the saliva is not stagnant (internal surface of the cheek, for example) in the case of buccal application], placing it by simple contact and if necessary applying slight pressure for a few seconds.

It should be added that the bioadhesive composition according to the invention may be withdrawn at any time in order to terminate the therapy when it is urgent to do so.

The buccal liquid (saliva) or nasal liquid penetrates into the composition and hydrates the polymers, leading to the formation of a matrix (or network); as the liquid continues to flow into this matrix, it dissolves the active constituent or constituents which are then progressively released. This release is continued substantially until the composition disappears or it becomes detached which, in the case of a tablet, normally occurs 4 to 8 hours after it has been set in place; in-vivo tests on Man and the dog carried out by the applicant revealed no irritation, pain nor excessive drying in the zone of application of the composition, showing that it is perfectly tolerated.

The following examples are given by way of non-limiting illustration of the present invention.

EXAMPLE 1

Composition in % by weight of a tablet (obtained by direct compression) for buccal application (for example in the dog or cat) for antisepsis of the buccal cavity, for example after an operation for removal of tartar or of a tooth, or for treatment against dental plaque:

| | |
|---|---|
| chlorhexidine acetate | 0.3 |
| CARBOPOL 934P | 15 |
| gelatin A | 35 |
| hydroxypropylmethyl cellulose | 22.5 |
| lactose (vehicle) | 25 |
| colloidal silica | 0.2 |
| glycerol behenate | 2 |

EXAMPLE 2

Composition in % by weight of a tablet (obtained by direct compression) for buccal application (for example in the cat) against aphthal or ulcerous pathologies:

| | |
|---|---|
| nicotinamide | 25 |
| CARBOPOL 934P | 15 |
| gelatin A | 35 |
| hydroxypropylmethyl cellulose | 22.8 |
| colloidal silica | 0.2 |
| glycerol behenate | 2 |

EXAMPLE 3

Composition in % by weight of a tablet (obtained by compression preceded by granulation) for buccal application in the dog or cat, particularly for treatment of aphthae appearing after abscesses:

| | |
|---|---|
| chlorhexidine acetate | 0.3 |
| nicotinamide | 25.20 |
| CARBOPOL 934P | 15.10 |
| gelatin A | 35.25 |
| hydroxypropylmethyl cellulose | 22.65 |
| hydrogenated ricin oil | 1 |
| glycerol behenate | 0.5 |

This composition is obtained by mixing in a homogeneous manner hydroxypropylmethyl cellulose (99 g), Carbopol 934P (66 g), gelatin A (154 g), nicotinamide (110 g) and chlorhexidine acetate (1.32 g). The mixture is wetted with a sufficient quantity of isopropyl alcohol (174 g), and the mixture thus obtained is granulated. The resultant granules are dried at 25° C. for 30 minutes, then forced through a grid with a mesh width of 1 mm. The granules passing through the grid then have added to them hydrogenated ricin oil, behenate of glycerol, and after mixing, compression is applied.

EXAMPLE 4

In-vitro study relating to the release kinetics of the active constituent.

This study was carried out by a dissolution test on a tablet in accordance with that obtained in Example 2 above.

More specifically, this test is carried out in a reactor containing 1 litre of Sorensen medium with a pH=6.8, and at 37° C., and equipped with a rotating plate. This apparatus conforms to the standards described in the European Pharmacopoeia 2nd edition (1991).

Samples were taken at regular intervals in the reactor, and were analysed by spectrophotometry of absorption in UV (wavelength: 262 nm).

The results (average for 3 tablets) were as follows:

| Time (minutes) | % of nicotinamide released |
|---|---|
| 0 | 0 |
| 60 | 40 |
| 120 | 60 |
| 180 | 70 |
| 240 | 80 |

EXAMPLE 5

In-vitro study relating to swelling of tablets. This study was carried out by submerging a tablet according to the invention in water at ambient temperature. It shows that the diameter of this tablet increased by a factor of only 0.25 after 6 hours of immersion, an increase which causes little discomfort in the mouth of the subject. As the volume of hydratation in situ is small, this swelling factor detected in vitro may be considered as a maximum value.

EXAMPLE 6

Industrial feasibility study of a tablet according to the invention.

A mixture of powders to be compressed must have good flow characteristics (regular flow ensures regularity and homogeneity of filling of the compression mold) and good cohesion properties.

The flow characteristics and suitability for compression were measured experimentally by producing tablets on an industrial compressing machine fitted with strain gauges (pressure measurement) and:

- monitoring effective filling of the compression mold by measuring the weight of the tablets, homogeneous weight being proof of good flow;
- measuring the hardness of the tablets formed, suitable hardness being a sign of sufficient cohesion, and
- checking whether ejection of the tablets is correct (non-adhesion to the die and absence of adhesive peak and seizing on registering the pressures).

The tests carried out on the compositions according to the invention, in a compressing machine and at an atmosphere of less than 50% relative humidity, led to obtaining tablets without defect; they do not adhere to the die, their weight is substantially constant (variations noted during three manufacturing sessions of 1 to 5 kg each are never above 2% by weight) and their hardness conforms with the values desired (approximately 100N).

What is claimed is:

1. Solid mucoadhesive therapeutic or hygienic composition for administration by application to the buccal or nasal mucous membrane, said composition comprising, in mixture, 15 to 25% by weight of a cellulosic ether selected from the group consisting of $C_1-C_4$ alkyl ethers of cellulose, $C_1-C_4$ hydroxyalkyl ethers of cellulose and mixtures thereof, said cellulosic ether being gelifiable when placed in the presence of an aqueous liquid, 10–15% by weight of a copolymer of acrylic acid and allyl sucrose or a physiologically acceptable salt of said copolymer, 30–45% by weight of a gelatin, and one or more therapeutic or hygienic active constituents.

2. Composition according to claim 1, wherein the gelatin is a type A gelatin which, in a 6.67% (w/v) aqueous solution, has a gel strength of 50 to 300 degrees Bloom.

3. Composition according to claim 1, wherein the gelatin has a particle size of less than 250 µm, and the copolymer or physiologically acceptable salt thereof has a particle size of 3 to 20 µm.

4. Composition according to claim 1, wherein the cellulosic ether is a hydroxypropyl cellulose or a hydroxypropylmethyl cellulose.

5. Composition according to claim 4, wherein the cellulosic ether has a viscosity measured at 20° C. in a 2% (w/v) aqueous solution of 10 to 75,000 mPa.s.

6. Composition according to claim 4, wherein the cellulosic ether has a particle size of less than 500 µm.

7. Composition according to claim 1, wherein the copolymer of acrylic acid and allyl sucrose has a viscosity measured at 25° C. in a 0.5% (w/v) aqueous solution of 300 to 400 mPa.s.

8. Composition according to claim 1, wherein said composition is in tablet form obtained by granulation with an organic solvent followed by compression.

9. Composition according to claim 1, wherein said composition is in tablet form obtained by mixing the cellulosic ether, copolymer of acrylic acid or physiologically acceptable salt thereof, gelatin and one or more therapeutic or hygienic active constituents followed by compression.

* * * * *